United States Patent
Berti et al.

(10) Patent No.: US 8,047,089 B2
(45) Date of Patent: Nov. 1, 2011

(54) DEVICE FOR THE OPTICAL MEASUREMENT OF A PRINTED SHEET AND METHOD FOR OPERATING THE DEVICE

(75) Inventors: Christopher Berti, Dielheim (DE); Hans Engler, Schriesheim (DE)

(73) Assignee: Heidelberger Druckmachinen AG, Heidelberg (DE)

( * ) Notice: Subject to any disclaimer, the term of this patent is extended or adjusted under 35 U.S.C. 154(b) by 517 days.

(21) Appl. No.: 11/943,197

(22) Filed: Nov. 20, 2007

(65) Prior Publication Data
US 2008/0115601 A1    May 22, 2008

(30) Foreign Application Priority Data
Nov. 20, 2006   (DE) .................. 10 2006 054 526

(51) Int. Cl.
*G01N 33/00* (2006.01)
(52) U.S. Cl. ........................................................ 73/866
(58) Field of Classification Search ............... 73/866
See application file for complete search history.

(56) References Cited

U.S. PATENT DOCUMENTS

| | | | |
|---|---|---|---|
| 4,495,149 A * | 1/1985 | Iwata et al. ............... | 73/864.25 |
| 4,505,589 A | 3/1985 | Ott et al. | |
| 5,152,516 A * | 10/1992 | Okayama et al. ............ | 271/3.13 |
| 6,571,620 B2 * | 6/2003 | Moisio ............................ | 73/159 |
| 6,772,689 B2 | 8/2004 | Endo et al. | |
| 2007/0113748 A1 | 5/2007 | Geissler et al. | |

FOREIGN PATENT DOCUMENTS

| | | |
|---|---|---|
| DE | 3932932 A1 | 4/1991 |
| DE | 4433707 A1 | 3/1995 |
| DE | 19530185 A1 | 5/1996 |
| DE | 102004015333 A1 | 10/2005 |
| DE | 102004021600 A1 | 12/2005 |
| EP | 0064024 B1 | 11/1982 |
| EP | 1190855 A1 | 3/2002 |
| GB | 2282105 A | 3/1995 |
| JP | 4-220345 A1 | 8/1992 |
| JP | 2004160871 A | 6/2004 |

* cited by examiner

*Primary Examiner* — Hezron E Williams
*Assistant Examiner* — Alex Devito
(74) *Attorney, Agent, or Firm* — Laurence A. Greenberg; Werner H. Stemer; Ralph E. Locher

(57) ABSTRACT

A device for the optical measurement of a printed sheet includes a measurement table with a displaceable measurement head. The measurement head is cleaned in a fully automatic or at least semi-automatic manner through the use of a cleaning device of the measurement table. A method for operating the device is also provided.

10 Claims, 1 Drawing Sheet

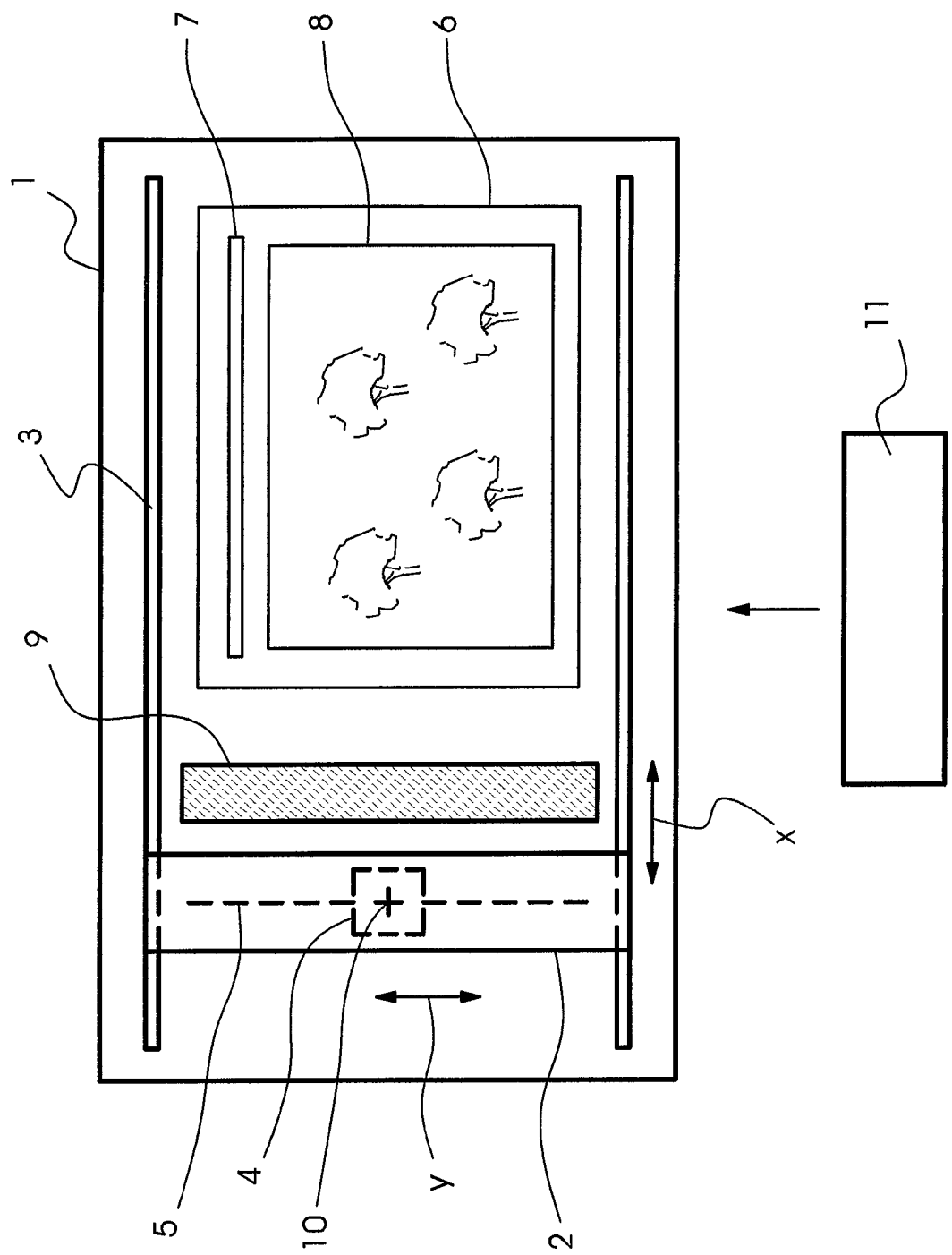

DEVICE FOR THE OPTICAL MEASUREMENT OF A PRINTED SHEET AND METHOD FOR OPERATING THE DEVICE

CROSS-REFERENCE TO RELATED APPLICATION

This application claims the priority, under 35 U.S.C. §119, of German Patent Application DE 10 2006 054 526.5, filed Nov. 20, 2006; the prior application is herewith incorporated by reference in its entirety.

BACKGROUND OF THE INVENTION

1. Field of the Invention

The present invention relates to a device for the optical measurement of a printed sheet and a method for operating the device. The device includes a measurement table with a movable measurement head.

Printed sheets are placed on a measurement table and scanned by a measurement head of the measurement table, for the purpose of monitoring print quality during an ongoing printing operation. Over the course of time, the optical system of the measurement head may become soiled, thus necessitating regular cleaning. The cleaning of the measurement head is a manual process that has many disadvantages.

On one hand, the avoidance of damage to the measurement head during the cleaning process is dependent on the operator's care. For example, there is a danger of the optical system being scratched, which might easily occur if it is cleaned inexpertly.

On the other hand, the operator is distracted from the running print job when he or she carries out the cleaning operation. However, it is desirable for the print job to be monitored continuously by the operator, in order for the operator to be able to intervene immediately in the event of a malfunction to limit the amount of waste.

European Patent EP 0 064 024 B1, corresponding to U.S. Pat. No. 4,505,589, for example, discloses a measurement table with the difficulties described above.

Such measurement tables require the removal of sample sheets from the delivery of the printing press in order to place them on the measurement table to carry out the measurement. Consequently, the measurement carried out with the aid of the measurement table positioned adjacent the press is performed offline.

There are also measurement devices that monitor print quality in-line in the printing press. German Published, Non-Prosecuted Patent Application DE 10 2004 021 600 A1, corresponding to U.S. Patent Application Publication No. US 2007/0113748, for example, describes an in-line measurement device including a measurement bar along which the measurement head is movable. The measurement bar may be open at the bottom or may be provided with a transparent cover at its underside.

If the measurement bar is open at the bottom, air is blown into the measurement bar. The air forms an air flow that emerges from the open underside and prevents dirt from entering the measurement bar. However, the air stream does not provide thorough cleaning.

If there is a transparent cover, it is cleaned manually through the use of a cleaning tool having a shape which matches the shape of the cover at least to reduce the risk of scratching the cover. The cleaning tool is not ideal, however, because there remains a risk of damage and because the operator's attention is no longer focused on the running print job.

BRIEF SUMMARY OF THE INVENTION

It is accordingly an object of the invention to provide a measurement device with a measurement table for the optical measurement of a printed sheet and a method for operating the device, which overcome the hereinafore-mentioned disadvantages of the heretofore-known devices and methods of this general type and which ensure thorough cleaning. In particular, it is an object of the invention to provide a device and method in which damage to a measurement head as a result of a cleaning operation is virtually impossible. It is additionally an object of the invention to provide a device and method in which the operator's attention can be focused entirely on monitoring a running printing operation.

With the foregoing and other objects in view there is provided, in accordance with the invention, a method for operating a device for the optical measurement of a printed sheet. The method comprises providing the device with a measurement table having a movable measurement head and a cleaning device, and fully automatically or at least semi-automatically cleaning the measurement head with the cleaning device.

With the objects of the invention in view, there is also provided a device for the optical measurement of a printed sheet. The device comprises a measurement table having a movable measurement head and a cleaning device. The cleaning device fully automatically or at least semi-automatically cleans the measurement head.

The method and device according to the invention ensure a reproducible thoroughness of the cleaning operation. Moreover, the avoidance of damage to the measurement head no longer depends on the skill of the operator. Such damage is now impossible. Furthermore, the cleaning of the measurement head now no longer requires the operator's attention so that the operator can focus his or her attention on monitoring the current printing operation.

In accordance with another feature of the invention, the measurement table has a cleaning area, the measurement head is supported so as to be movable into the cleaning area and the cleaning device is disposed in the cleaning area so that the measurement head may be moved to the cleaning area and be cleaned there through the use of the cleaning device. The cleaning area may be located on a table plate of the measurement table, adjacent a placement area disposed thereon. The printed sheet is placed on the placement area and fixed thereon for the measurement. The cleaning area and the placement area may also be identical to each other. In this case, the cleaning device may be formed by a cleaning sheet that is placed on the measurement table instead of the sample sheet to be measured. This cleaning sheet may, for example, be formed of a fabric, fleece, or foamed material wetted with a cleaning liquid.

In accordance with a further feature of the invention, the measurement head may be supported to be movable relative to the cleaning device during the cleaning operation, so that the measurement head is moved relative to the cleaning device during cleaning. Thus the cleaning device can be stationary and there is no need for additional drives provided exclusively for the cleaning operation. The cleaning operation relies on using the intrinsic mobility of the measurement head and the drive that drives the displacement movement.

The stationary cleaning device may, for example, be a cleaning roller that rotates about its axis of rotation, which is stationary during cleaning. Instead of the cleaning roller, a cleaning tape may be used. The cleaning tape may be endless and wrap around deflection rollers that rotate about their stationary axes of rotation during cleaning. The cleaning tape may also be a finite belt that is unwound from an unwinding reel and wound onto a wind-up reel during cleaning of the measurement head. The axes of rotation of the two reels may be stationary during cleaning.

In one case, the relative movement between the cleaning device and the measurement head may be implemented by the displacement movement of the measurement head and a simultaneous movement the cleaning device. In another case, the relative movement may be implemented by moving only the cleaning device. The former case is present, for example, if the cleaning device is embodied as a cleaning roller as mentioned above, with the relative movement resulting from superposing the displacement movement of the measurement head and the rotary movement of the cleaning roller. The latter case is present, for example, if the cleaning device is embodied as a blown-air or blast-air nozzle that is provided in the cleaning area to blast away dirt from the measurement head. In this case, the relative movement between the measurement head and the blast-air nozzle takes the form of the displacement movement of the measurement head, which may be displaced above the blast-air nozzle in such a way that the blast air directed against the measurement head from below successively passes over the measurement head sections that are to be cleaned.

Touch-free cleaning of the measurement head is possible not only through the use of the blast-air nozzle, but also through the use of an ultrasound emitter provided in the cleaning area.

In accordance with an added feature of the invention, the measurement table may be constructed as a two-coordinate measurement table with an imaginary x-axis and an imaginary y-axis. The measurement head is supported so as to be displaceable into the cleaning area along the x-axis and to be movable along the y-axis relative to the cleaning device during cleaning. Accordingly, when the measurement head is displaced into the cleaning zone, it moves along the x-axis of the measurement table. When the measurement head is being cleaned, it moves relative to the cleaning device along the y-axis of the measurement table. The x-axis and the y-axis are located in the plane of the table plate of the measurement table and are substantially horizontal axes. A possible slight inclination of the table plate is neglected.

Of course, the measurement table may include an imaginary z-axis in addition to the x-axis and the y-axis that are perpendicular to each other. The measurement head may be movable along the imaginary z-axis, which is a substantially vertical axis. The movement of the measurement head along the z-axis may serve to engage and disengage the measurement head with and from the cleaning device. The movement of the measurement head along the z-axis may also serve to set the required distance between the printed sheet to be measured and the measurement head for the measurement.

It is also conceivable to create the movement of the measurement head relative to the cleaning device in the cleaning area by superposing a movement of the measurement head along the x-axis and a simultaneous movement of the measurement head along the y-axis. The movement resulting from the superposition may, for example, be a zigzag movement or a meandering movement of the measurement head over the aforementioned cleaning sheet. The movement resulting from the superposition may, however, also be a helical movement of the measurement head over the blast air nozzle so that the blast air drives the dirt from the center of the area of the measurement head to be cleaned to the edges thereof.

In accordance with an additional feature of the invention, the cleaning device may be a scraper for scraping contaminants off the measurement head. In this context, provision may be made for the cleaning device to scrape the dirt off the measurement head due to the movement of the measurement head relative to the cleaning device. If the cleaning device is constructed as a scraper, the cleaning device touches the measurement head during the scraping operation. The scraping off of the contaminants may be carried out as a wet and/or dry process.

For example, a wet cleaning operation, i.e. a washing operation, is carried out on the measurement head through the use of the cleaning device in the case of the aforementioned embodiment of the cleaning device as a cleaning sheet wetted with a cleaning liquid.

The measurement head and its optical system may be washed and subsequently rubbed dry, for example, through the use of a cleaning sheet that includes a damp portion wetted with the cleaning liquid and a dry portion that has not been wetted with the cleaning liquid.

An exclusively dry cleaning operation, i.e. a dusting off of the measurement head, may, for example, be carried out through the use of the aforementioned cleaning roller if the latter is constructed as a type of plush roller with a high dust-binding effect.

The measurement head may be a scanning densitometer or a color measurement device, for example a colorimeter or a spectrometer, and may carry out its measurement within a control strip printed on the printed sheets specifically for this purpose, or within the actual printed image on the printed sheets (printed-image inspection).

Other features which are considered as characteristic for the invention are set forth in the appended claims.

Although the invention is illustrated and described herein as embodied in a device for the optical measurement of a printed sheet and a method for operating the device, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE DRAWING

The figure of the drawing is a diagrammatic, top-plan view of a measurement table carrying a printed sheet, as well as an electronic control device.

DETAILED DESCRIPTION OF THE INVENTION

Referring now in detail to the single figure of the drawing, there is seen a measurement table 1. A printed sheet 6, which is also referred to as a sample sheet, to be examined and measured in terms of print quality, rests on the measurement table 1. The measurement table 1 includes a measurement bar 2, which is movable along rails 3 in a direction x. The measurement bar 2 also includes a measurement head 4, which is movable in a direction y along a rail 5 provided on the measurement bar 2. In addition, an axis 10 is disposed on the measurement bar 2. The measurement head 4 is also movable in a direction perpendicular to the image plane of the figure, i.e. towards and away from the printed sheet 6, along the axis 10. Drives for driving the displacement movements of the measurement bar 2 and the measurement head 4 are controlled by an electronic control device 11, but are not illustrated for reasons of clarity.

The measurement head 4 has an optical system that is sensitive to contamination and is used to measure a printed image 8 or a control strip 7 printed next to the image on the printed sheet 6 in densitometric or colorimetric terms.

A cleaning device 9 forms a cleaning area disposed adjacent the printed sheet 6. The cleaning device 9 is a strip of soft, resilient, absorbent fabric or fleece wetted with a cleaning liquid.

The illustrated system operates as follows: If a non-illustrated sensor for detecting contamination on the optical system of the measurement head 4 signals to the control device 11 that the contamination has exceeded a defined limit, the control device 11 alerts the operator of the printing press associated with the measurement table 1, for example through the use of a red warning light, so that the operator can access a cleaning program on the control device 11 for washing the measurement head 4. It is also possible for the control device 11 to automatically initiate the cleaning program in reaction to the sensor signal.

In both cases, in accordance with the cleaning program, the measurement bar 2 and the measurement head 4 are moved along the rails 3, 5 into a position in which the measurement head 4 is located directly above the cleaning device 9. In a subsequent program step, the measurement head 4 is lowered along the axis 10 until it rests against the cleaning device 9.

Then the measurement head 4 is moved back and forth multiple times along the rail 5 from one end of the cleaning device 9 to the other. In the process, the optical system of the measurement head 4 is wiped and cleaned by the cleaning device 9. In the process, the measurement bar 2 may move into the x direction at minimum speed in order for the measurement head to carry out a zigzag-shaped or sinusoidal oscillation on the cleaning device 9.

The material properties of the cleaning device and the form of the movement of the measurement head 4 ensure that the dirt is transferred from the measurement head 4 to the cleaning device 9 and not re-transferred from the latter to the former.

In a last step, the measurement head 4 is lifted off the cleaning device 9 along the axis 10 and subsequently moved back along the x and y directions into the position required for measuring the printed sheet 6.

The cleaning program may include a short waiting period between the end of the cleaning operation and the beginning of the measurement of the printed sheet 6, to allow the remains of the cleaning liquid on the optical system to evaporate. Once the waiting period is over, the control device 11 initiates the measuring operation or signals to the operator, through the use of a green ready light, that he or she can start the measuring operation by pressing a button.

It is also possible for various cleaning programs to be stored in the control device 11. Among them, the one suitable for the respective degree of soiling of the measurement head 4 may be selected and executed.

The cleaning device 9 may be a disposable item and may be replaced by a new cleaning device 9 once the cleaning operation has been completed.

The invention claimed is:

1. A method for operating a device for the optical measurement of a printed sheet, the method comprising the following steps:
    optically measuring a printed sheet with the device including a measurement table having a movable measurement head and a cleaning device; and
    fully automatically or at least semi-automatically cleaning an optical system of the measurement head with the cleaning device;
    moving the measurement head into a cleaning area, and cleaning the optical system in the cleaning area with the cleaning device, the cleaning area being located adjacent a placement area for placement of the printed sheet on the measurement table;
    placing the printed sheet at rest on the placement area during measurement of the printed sheet.

2. The method according to claim 1, which further comprises moving the measurement head relative to the cleaning device during the cleaning of the optical system.

3. The method according to claim 2, which further comprises displacing the measurement head into the cleaning area along an x-axis of the measurement table, and moving the measurement head relative to the cleaning device along a y-axis of the measurement table during cleaning of the optical system.

4. The method according to claim 2, which further comprises scraping dirt off the optical system with the cleaning device due to movement of the measurement head relative to the cleaning device.

5. The method according to claim 3, which further comprises scraping dirt off the optical system with the cleaning device due to movement of the measurement head relative to the cleaning device.

6. A device for the optical measurement of a printed sheet, the device comprising:
    a measurement table having a movable measurement head, a cleaning device, a placement area for accepting the printed sheet at rest during measurement of the printed sheet, and a cleaning area in which said cleaning device is disposed, said cleaning area being disposed adjacent said placement area, said measurement head having an optical system, said measurement head being supported for displacement into said cleaning area, said cleaning device fully automatically or at least semi-automatically cleaning said optical system.

7. The device according to claim 6, wherein said measurement head is supported for movement relative to said cleaning device during the cleaning of said optical system.

8. The device according to claim 6, wherein said measurement head is supported for movement relative to said cleaning device during the cleaning of said optical system.

9. The device according to claim 8, wherein said measurement table is a two-coordinate measurement table with an x-axis and a y-axis, said measurement head is supported for displacement into said cleaning area along said x-axis and for movement relative to said cleaning device along said y-axis during cleaning of said optical system.

10. The device according to claim 6, wherein said cleaning device is a scraper for scraping dirt off said optical system.

* * * * *